United States Patent
Aldritt et al.

(10) Patent No.: US 7,919,126 B2
(45) Date of Patent: Apr. 5, 2011

(54) EFFERVESCENT COMPOSITION AND METHOD OF MAKING AN EFFERVESCENT COMPOSITION INCLUDING A VISCOUS COMPONENT

(75) Inventors: Mary Aldritt, Excelsior, MN (US); Fred Wehling, Greenfield, MN (US); Robert E. Lee, St. Louis Park, MN (US)

(73) Assignee: Amerilab Technologies, Inc., Plymouth, MN (US)

( * ) Notice: Subject to any disclaimer, the term of this patent is extended or adjusted under 35 U.S.C. 154(b) by 0 days.

(21) Appl. No.: 12/330,193

(22) Filed: Dec. 8, 2008

(65) Prior Publication Data

US 2009/0087386 A1    Apr. 2, 2009

Related U.S. Application Data

(62) Division of application No. 10/963,222, filed on Oct. 12, 2004, now Pat. No. 7,507,396.

(60) Provisional application No. 60/512,173, filed on Oct. 17, 2003.

(51) Int. Cl.
*A61K 36/67* (2006.01)
*A61K 36/00* (2006.01)
*A61K 35/24* (2006.01)
*A61K 35/37* (2006.01)
*A61K 9/46* (2006.01)

(52) U.S. Cl. ......... 424/734; 424/725; 424/537; 424/466

(58) Field of Classification Search .................. None
See application file for complete search history.

(56) References Cited

U.S. PATENT DOCUMENTS

| | | | |
|---|---|---|---|
| 1,450,865 A | 4/1923 | Pelc | |
| 2,868,646 A * | 1/1959 | Schapiro | 426/96 |
| 2,985,562 A | 5/1961 | Millard et al. | |
| 4,049,834 A | 9/1977 | Barwald et al. | |
| 4,082,858 A | 4/1978 | Morita et al. | |
| 4,127,645 A | 11/1978 | Witzel et al. | |
| 4,147,768 A | 4/1979 | Shaffer et al. | |
| 4,267,164 A | 5/1981 | Yeh et al. | |
| 4,289,751 A | 9/1981 | Windheuser | |
| 4,552,771 A | 11/1985 | Fülberth et al. | |
| 4,599,403 A | 7/1986 | Kumar et al. | |
| 4,946,691 A | 8/1990 | Burkhardt et al. | |
| 5,112,610 A | 5/1992 | Kienle | |
| 5,171,571 A | 12/1992 | Stephan et al. | |
| 5,252,341 A | 10/1993 | Sauerbier et al. | |
| 5,516,529 A | 5/1996 | Zellweger | |
| 5,609,883 A * | 3/1997 | Valentine et al. | 424/464 |
| 5,707,654 A | 1/1998 | Béres et al. | |
| 5,762,961 A | 6/1998 | Roser et al. | |
| 5,783,235 A | 7/1998 | Ting et al. | |
| 5,925,378 A | 7/1999 | Carnazzo | |
| 5,993,854 A | 11/1999 | Needleman et al. | |
| 6,071,539 A | 6/2000 | Robinson et al. | |
| 6,140,414 A | 10/2000 | Ohsawa et al. | |
| 6,197,338 B1 | 3/2001 | Nürnberg et al. | |
| 6,214,386 B1 | 4/2001 | Santus et al. | |
| 6,280,775 B1 | 8/2001 | Sasson et al. | |
| 6,506,713 B1 | 1/2003 | Slavtcheff et al. | |
| 2002/0086062 A1 | 7/2002 | Kuhrts | |
| 2004/0115307 A1 | 6/2004 | Boyd | |

FOREIGN PATENT DOCUMENTS

| | | |
|---|---|---|
| DE | 10001945 | 7/2001 |
| WO | WO 9503785 A1 | 2/1995 |
| WO | WO 02098388 A2 | 12/2002 |

OTHER PUBLICATIONS

"Excipients: What is a lubricant?". Internet Archive Date: Feb. 10, 2002 [Retrieved from the Internet on: Mar. 19, 2010]. Retrieved from: <http://web.archive.org/web/20021021004151/http://pformulate.com/lubricants.htm>.*
Jackson Gastroenterology, "Calcium carbonate, magnesium carbonate," http://www.gicare.com/pated/mylanta_gelcaps.htm, 2002.

* cited by examiner

*Primary Examiner* — Amy L Clark
(74) *Attorney, Agent, or Firm* — Allison Johnson, P.A.

(57) ABSTRACT

Disclosed is an effervescent composition that includes a viscous component is in the form of a free flowing granulation, a tablet made from the free flowing granulation, and a method of using the effervescent composition.

12 Claims, No Drawings

EFFERVESCENT COMPOSITION AND METHOD OF MAKING AN EFFERVESCENT COMPOSITION INCLUDING A VISCOUS COMPONENT

CROSS-REFERENCE TO RELATED APPLICATIONS

This application is a divisional of U.S. patent application Ser. No. 10/963,222 filed on Oct. 12, 2004, now U.S. Pat. No. 7,507,396, which claims the benefit of U.S. Provisional Application No. 60/512,173, filed Oct. 17, 2003, both of which are incorporated herein.

BACKGROUND

The invention relates to incorporating a viscous component in an effervescent composition.

Viscous materials are difficult to formulate into a homogeneous effervescent composition that is easy to handle and package. In particular, viscous materials can cause aggregation, which impairs the formation of a free flowing effervescent powder. Viscous materials also stick to the equipment that is used to process effervescent compositions including the tablet presses that are used to mass-produce tablets. Attempts to form tablets from compositions that include viscous agents can produce deformed tablets that lack structural integrity.

SUMMARY

In one aspect, the invention features a method of making an effervescent composition, the method including heating a viscous component to a temperature of at least 45° C., the viscous component exhibiting a viscosity greater than 50,000 cps at 23° C. and 1 $sec^{-1}$ and a viscosity less than 5000 cps at a temperature of at least 38° C. and 1 $sec^{-1}$, heating a composition including an effervescent agent to a temperature of at least 45° C., and combining the heated viscous component and the heated composition. In one embodiment, the viscous component is selected from the group consisting of honey, molasses, wax and combinations thereof. In other embodiments, the viscous component includes hop extract. In another embodiment, the viscous component includes kava.

In one embodiment, the effervescent composition includes from 5% by weight to 30% by weight of the viscous component. In another embodiment, the effervescent composition includes from about 5% by weight to about 25% by weight of the viscous component. In other embodiments, the effervescent composition includes from about 10% by weight to about 20% by weight the viscous component.

In some embodiments, the effervescent composition further includes a flow agent. In one embodiment, the flow agent is selected from the group consisting of silica, fumed silica, precipitated silica, magnesium oxide, calcium phosphate, magnesium carbonate, calcium silicate, sodium alumino silicate, and combinations thereof.

In other embodiments, the effervescent composition includes from 3% by weight to 20% by weight silica, or even from 5% by weight to 15% by weight silica.

In another aspect, the invention features a method of making a free flowing powder that includes an effervescent composition disclosed herein.

In other aspects, the invention features a method of making an effervescent tablet, the method including making an effervescent composition, and tableting the effervescent composition. In one embodiment, the tableting includes forming a tablet having a hardness of from 3 Kp to 15 Kp. In other embodiments, the tablet includes from 5% by weight to 30% by weight of the viscous component. In some embodiments, the tablet includes from about 10% by weight to about 20% by weight of the viscous component.

In another embodiment, the tablet further includes binder and lubricant.

In one embodiment, the method of making an effervescent composition, includes heating a viscous component having a viscosity greater than 50,000 cps at 23° C. to a temperature sufficient to cause the component to exhibit a viscosity no greater than 5000 cps, heating a composition including an effervescent agent to a temperature of at least 45° C., and combining the component and the heated effervescent agent to form an effervescent composition.

In another aspect, the invention features an effervescent composition that includes a viscous component exhibiting a viscosity greater than 50,000 cps at 23° C. and 1 $sec^{-1}$ and no greater than 5000 cps at a temperature of at least 38° C. and 1 $sec^{-1}$, effervescent agent, and silica, the effervescent composition being a uniform, free-flowing granulation. In some embodiments, the effervescent composition includes from 3% by weight to 20% by weight silica.

In another embodiment, the effervescent composition includes a viscous component exhibiting a viscosity greater than 50,000 cps at 1 $sec^{-1}$ and 23° C. and a viscosity less than 5000 cps at 10 $sec^{-1}$ and a temperature of at least 55° C., and effervescent agent. In one embodiment, the viscous component is solid at 23° C. In another embodiment, the effervescent composition is a uniform, free-flowing granulation. In some embodiments, the effervescent composition includes from 5% by weight to 30% by weight the viscous component, from about 5% by weight to about 25% by weight of the viscous component, or even from about 10% by weight to about 20% by weight of the viscous component. In some embodiments, the effervescent composition includes a flow agent selected from the group consisting of silica, fumed silica, precipitated silica, magnesium oxide, calcium phosphate, magnesium carbonate, calcium silicate, sodium alumino silicate, and combinations thereof.

In some embodiments, an effervescent composition described herein is in the form of a tablet. In one embodiment, the composition of the tablet further includes binder, lubricant, or a combination thereof. In another embodiment, the effervescent composition described herein is in the form of a free flowing powder. In another embodiments, an effervescent composition described herein includes an effervescent agent that includes citric acid and sodium bicarbonate, and further includes silica, lactose, magnesium stearate, and sorbitol.

In another aspect, the invention features a method of using an effervescent composition described herein, the method including adding the effervescent composition to an aqueous liquid.

The invention features a method of incorporating a viscous component in an effervescent composition. The effervescent composition provides a viscous component in a predetermined amount and in a convenient form that is easy to handle.

The invention also features an effervescent composition that is capable of being tableted in an automated process and forming a tablet that exhibits good structural integrity.

The effervescent composition can be formulated to readily disperse in aqueous-based compositions. The effervescent composition can be formulated to disperse the viscous component in water at a rate that is faster relative to the rate of dispersion of the viscous component alone.

Other features and advantages will be apparent from the following description of the preferred embodiments and from the claims.

GLOSSARY

In reference to the invention, these terms have the meanings set forth below:

The term "effervescent composition" refers to a composition that evolves a gas (e.g., carbon dioxide) when placed in an aqueous liquid.

The term "viscous component" refers to a component that is any one of a solid, semisolid and liquid at room temperature.

DETAILED DESCRIPTION

The effervescent composition includes a viscous component, and an effervescent agent. The viscous component is a solid, semisolid or has a viscosity of at least 50,000 centipoise (cps), at least 100,000 cps, or even at least 300,000 cps, at room temperature (i.e., from 68° F. to 77° F. (20° C. to 25° C.), and is a pourable liquid when heated to an elevated temperature. Preferably the viscous component exhibits a viscosity no greater than 5000 cps, or even no greater than 3000 cps at a temperature of at least 40° C., at least 55° C., or even at least 60° C., when measured at 10 second$^{-1}$ (reciprocal second), or even 1 sec$^{-1}$.

Suitable viscous components include Newtonian and non-Newtonian compounds including, e.g., honey, molasses, wax, hop extract, kava, and mixtures thereof. A suitable hop extract is available under the trade designation YC Enhanced Oil hop extract from Yakima Chief, Inc. (Sunnyside, Wash.), one lot of which was found to have a viscosity of 54,000 cps at 23° C. and 1 sec$^{-1}$ and 8,400 cps at 23° C. and 10 sec$^{-1}$ and 2,900 at 40° C. and 1 sec$^{-1}$ and 700 cps at 40° C. and 10 sec$^{-1}$. The viscous component is present in the effervescent composition in an amount suitable for its intended purpose. Useful formulations include a viscous component in an amount of at least 1% by weight, from about 5% by weight to about 30% by weight, from about 5% by weight to about 25% by weight, or even from about 10% by weight to about 20% by weight.

The effervescent agent preferably is at least one component of an effervescent couple that includes an acid and a base. The effervescent couple is activated when contacted with water, e.g., when the tablet is placed in a glass of water. The water liberates the acid and base and enables the acid and base to react with each other to produce carbon dioxide gas, which imparts carbonation to the aqueous composition. At least one component of the effervescent couple can also be an active agent. Examples of useful acids include citric acid, ascorbic acid, malic acid, adipic acid, tartaric acid, fumaric, succinic acid, sodium acid pyrophosphate, lactic acid, hexamic acid, and acid salts and acid anhydrides thereof, and mixtures thereof. Examples of useful acid anhydrides include citraconic anhydride, glucono-D-lactone, and succinic anhydride. Examples of useful acid salts include potassium bitartrate, acid citrate salts, sodium dihydrogen phosphate, disodium dihydrogen phosphate, sodium acid sulfite, and combinations thereof. Acid is present in the composition in an amount of from 5% by weight to about 60% by weight, from about 5% by weight to about 30% by weight, or even from about 10% by weight to about 20% by weight.

The base preferably is capable of generating carbon dioxide. Examples of suitable carbonate bases include sodium bicarbonate, sodium carbonate, sodium sesquicarbonate, potassium carbonate, potassium bicarbonate, calcium carbonate, magnesium carbonate, magnesium oxide, sodium glycine carbonate, L-lysine carbonate, arginine carbonate, zinc carbonate, zinc oxide and mixtures thereof. The base is present in the composition in an amount of from 10% by weight to about 60% by weight, from about 20% by weight to about 50% by weight, or even from about 30% by weight to about 45% by weight.

The effervescent composition preferably includes a flow agent. The flow agent preferably enhances the ability of the effervescent composition to flow through the components of a manufacturing operation including, e.g., the components of an automated tableting operation (e.g., a hopper and a tablet press). Suitable flow agents include, e.g., silica (e.g., fumed silica and precipitated silica), magnesium oxide, calcium phosphates (e.g., mono-, di- and tri-calcium phosphates), magnesium carbonate, calcium silicate, sodium alumino silicates, and combinations thereof. A useful fumed silica is commercially available under the trade designation CAB-O-SIL from Cabot Corp. (Boston, Mass.). The flow agent is preferably present in the composition in an amount of at least 0.5% by weight, from about 3% by weight to about 20% by weight, or even from about 5% by weight to about 15% by weight.

The effervescent composition can be in a variety of forms including, e.g., powder (e.g., a free flowing granulation), tablet, capsule, and pellet. The effervescent composition can be prepared to exhibit a desired dissolution rate. Useful effervescent tablets include effervescent tablets having a hardness of at least 3 kiloponds (Kp), at least 4 Kp, from about 5 Kp to about 15 Kp, or even from about 5 Kp to about 10 Kp, as measured on a standard hardness tester fitted with a strain gauge. In one embodiment, the tablets are formulated to weigh about 5000 mg and preferably dissolve in excess boiling water in less than 300 seconds, less than 100 second, or even less than 60 seconds.

When in the form of a tablet or capsule, the composition preferably includes binder, lubricant, and combinations thereof. Examples of suitable binders include, e.g., starches, natural gums, cellulose gums, microcrystalline cellulose, methylcellulose, cellulose ethers, sodium carboxymethylcellulose, ethylcellulose, gelatin, dextrose, lactose, sucrose, sorbitol, mannitol, polyethylene glycol, polyvinylpyrrolidone, pectins, alginates, polyacrylamides, polyvinyloxoazolidone, polyvinylalcohols and mixtures thereof.

The effervescent composition includes a sufficient amount of binder to assist in holding the components of the composition together in the form of a tablet. Preferably binder is present in the composition in an amount of from 10% by weight to about 60% by weight, from about 15% by weight to about 50% by weight, or even from about 25% by weight to about 40% by weight.

Various lubricants are suitable including water dispersible, water soluble, water insoluble lubricants and combinations thereof. Preferred lubricants are water soluble. Examples of useful water soluble lubricants include sodium benzoate, polyethylene glycol, L-leucine, adipic acid, and combinations thereof. The composition can also include water insoluble lubricants including, e.g., stearates (e.g., magnesium stearate, calcium stearate and zinc stearate), oils (e.g., mineral oil, hydrogenated and partially hydrogenated vegetable oils, and cotton seed oil) and combinations thereof. Other water insoluble lubricants include, e.g., animal fats, polyoxyethylene monostearate, talc, and combinations thereof.

The effervescent composition preferably includes a sufficient amount of lubricant to enable the composition to be formed into tablets and released from a high speed automated tableting press in the form of a tablet. The effervescent composition preferably includes water soluble lubricant in an amount of from 0.1% by weight to about 15% by weight, from about 0.1% by weight to about 10% by weight, from about 0.5% by weight to about 5% by weight, or even from about 0.5% by weight to about 3% by weight.

The effervescent composition can also include water insoluble lubricants. Preferably effervescent composition includes less than 3% by weight water insoluble lubricants.

The effervescent composition can also include other ingredients including, e.g., flavor agents, fillers, surfactants (e.g., polysorbate 80 and sodium lauryl sulfate), color agents including, e.g., dyes and pigments, sweetening agents, and combinations thereof.

In preparing the effervescent composition at least some of the components are preferably heated to a temperature of at least 40° C., from 40° C. to 70° C., or even from 45° C. to 65° C., prior to being combined with one or more of the other components of the effervescent composition. In some embodiments, the viscous component is stirred (e.g., subjected to a shear stress) prior to combination with another component of the effervescent composition.

The effervescent composition is preferably stored in a moisture-proof package e.g., sealed foil containers (e.g., bags and pouches), sealed plastic bags, blister packs, desiccant capped tubes, and combinations thereof. A number of tablets or capsules can be placed in a single package.

The effervescent composition can be formulated for use in a variety of applications including, e.g., dispersing in an aqueous-based composition (e.g., water) at a variety of temperatures (e.g., refrigerated, room temperature, and boiling (e.g., boiling water)).

The invention will now be described by way of the following examples.

EXAMPLES

Test Procedures

Test procedures used in the examples include the following.

Viscosity

The viscosity measurement is obtained using a Haake RS100 controlled stress rheometer (Haake). The rheometer is set up with a parallel plate measuring system in which the bottom plate is fixed and the temperature of the sample is controlled using a TC-81 Peltier temperature controller. The upper plate is 35 mm diameter and is rotated at a programmed ramp from 0 $sec^{-1}$ to 50 $sec^{-1}$ shear rate and then from 50 $sec^{-1}$ to 0 $sec^{-1}$ shear rate. The sample is tested by placing a from 2 to 3 cubic centimeters of sample on the bottom plate and raising the bottom plate until the gap to the upper plate is 2 mm. The sample completely fills the gap between the two plates and excess is carefully scraped away. The samples are equilibrated to the specified temperature before the measurement is obtained. A solvent trap apparatus is employed to minimize evaporation at higher temperatures. Viscosity values are determined during the ramp down from 50 $sec^{-1}$ to 0 $sec^{-1}$ at shear rates of 1 $sec^{-1}$ and 10 $sec^{-1}$.

Example 1

The effervescent composition of Example 1, which included hops extract having a viscosity of 54,000 cps at 23° C. and 1 $sec^{-1}$ and 8,400 cps at 23° C. and 10 $sec^{-1}$ and 2,900 at 40° C. and 1 $sec^{-1}$ and 700 cps at 40° C. and 10 $sec^{-1}$, was prepared as follows. Into a first container was blended 29.7 kg anhydrous citric acid fine granular 50 USP/FCC, and 26.4 kg instant sorbitol FGPh, and 2,200 g magnesium stearate. Into a second container was blended 37.4 kg sodium carbonate (Grade 50), 37.4 kg sodium carbonate (Grade 100), 7,700 g sodium bicarbonate No. 5, and 28.6 kg FAST-FLO spray dried modified lactose monohydrate (#316 NF) Foremost Farms (Rothschild, Wis.). The first and second containers were placed in an oven, preheated to 50° C.+/−2° C., for at least 14 hours prior to further compounding.

The heated contents of the second container were added to a ribbon blender, which had been preheated to 50° C.+/−2° C. using belt heaters, followed by the addition of 15.4 kg CAB-O-SIL fumed silicon dioxide (Cabot Corp., Boston, Mass.), and then the contents of the first container. The components were blended for 30 minutes with the cover of the blender closed. Then 35.2 kg YC Enhanced Oil hop extract (Yakima Chief, Inc., Sunnyside, Wash.), which had been warmed in a warming vessel, was added slowly to the ribbon blender. The mixture was blended for from about 30 to 60 minutes.

The resulting composition was a uniform, free-flowing granulation that did not stick to the sides of the blender.

The effervescent composition was then transferred to a tablet press having a one inch tool to form tablets weighing from approximately 4.75 g to 5.25 g. The tablets were pressed to a hardness of from 3 Kp to 9 Kp.

The tablets had an average weight of 5.02 g, a thickness of 0.256 inch, and a hardness of 7.0 Kp.

Two tablets were then placed in 200 mL of boiling water and were observed to completely dissolve in 163 seconds.

Example 2

An effervescent composition including kava was prepared by adding 137.5 g kava extract containing stevia (the kava had a viscosity of 14,000 cps at 55° C. and 1 $sec^{-1}$ and 4,500 cps at 55° C. and 10 $sec^{-1}$), which had been preheated to a temperature of 60° C., to a composition that had been preheated to 60° C. and included 467.5 g sodium carbonate #100, 220 g citric acid, 165.0 g FASTFLO spray dried modified lactose monohydrate (#316 NF) Foremost Farms (Rothschild, Wis.), 220 g sorbitol, 103.1 g CAB-O-SIL silicon dioxide (Cabot Corp., Boston, Mass.), 48.1 g sodium bicarbonate #5, and 13.8 g magnesium stearate. The kava was added to the mixture over a period of 90 seconds. The mixing and heating were maintained for ten minutes. The composition was then cooled to room temperature. The composition was a uniform, free-flowing granulation.

The effervescent composition of Example 2 was then formed into tablets on a hand press. The tablets had a mass ranging from 5.05 g to 5.24 g, a thickness of from 0.322 inch to 0.330 inch and a hardness of from 5.0 Kp to 5.5 Kp. The tablets, when placed in 200 mL of room temperature water, were observed to form a cloudy composition having a yellow residue after 15 minutes.

Other embodiments are within the claims.

What is claimed is:

1. An effervescent composition comprising:
   from about 5% by weight to 25% by weight of a viscous component exhibiting a viscosity greater than 50,000 cps at 23° C. and a shear rate of 1 $sec^{-1}$ and a viscosity less than 5000 cps at a temperature of at least 38° C. and a shear rate of 1 $sec^{-1}$, and said viscous component is selected from the group consisting of hops extract, kava, molasses, honey, or a combination thereof;
   an effervescent agent comprising an acid and a base; and
   from about 3% by weight to about 20% by weight of a flow agent selected from the group consisting of silica, fumed silica, precipitated silica, magnesium oxide, calcium phosphate, magnesium carbonate, calcium silicate, sodium alumino silicate, or a combination thereof, and said effervescent composition is in the form of a uniform, free flowing granulation.

2. The effervescent composition of claim 1, wherein said viscous component comprises hops extract.

3. The effervescent composition of claim 2, comprising from about 10% by weight to about 20% by weight of the hops extract.

4. The effervescent composition of claim 2 further comprising a binder, a lubricant, or a combination thereof.

5. The effervescent composition of claim 1, wherein said flow agent comprises from about 3% by weight to about 20% by weight silica.

6. The effervescent composition of claim 1, wherein said flow agent comprises from about 5% by weight to about 15% by weight silica.

7. The effervescent composition of claim 2, wherein said effervescent agent comprises citric acid and sodium bicarbonate, and said effervescent composition further comprises:
   lactose;
   magnesium stearate; and
   sorbitol.

8. A tablet comprising the effervescent composition of claim 2, said tablet having a hardness of at least 3 kiloponds and disintegrating in boiling water in less than 300 seconds.

9. The tablet of claim 8 having a hardness of from about 5 kiloponds to about 15 kiloponds.

10. An effervescent tablet comprising:
    from about 5% by weight to 25% by weight of a viscous component selected from the group consisting of hops extract, kava, molasses, honey, or a combination thereof;
    an effervescent agent comprising an acid and a base; and
    from about 3% by weight to about 20% by weight of a flow agent selected from the group consisting of silica, fumed silica, precipitated silica, calcium silicate, sodium alumino silicate, or a combination thereof,
    and said effervescent tablet comprises a uniform composition, has a hardness of from about 5 kiloponds to about 15 kiloponds, and disintegrates in boiling water in less than 300 seconds.

11. The effervescent tablet of claim 10 further comprising at least one of a binder and a lubricant.

12. The effervescent tablet of claim 10, wherein said effervescent agent comprises citric acid and at least one of sodium bicarbonate and potassium bicarbonate, and said effervescent tablet further comprises:
    lactose;
    magnesium stearate; and
    sorbitol.

* * * * *